United States Patent [19]

Zandberg et al.

[11] Patent Number: 5,713,663
[45] Date of Patent: Feb. 3, 1998

[54] METHOD AND APPARATUS FOR MIXING CONCRETE IN A CONCRETE MIXING DEVICE TO A SPECIFIED SLUMP

[75] Inventors: Henry Zandberg, Victoria; Hussein Briedis, St Cheltenham, both of Australia

[73] Assignee: Boral Resources (VIC) PTY Limited, Malvern, Australia

[21] Appl. No.: 647,834

[22] Filed: May 15, 1996

[30] Foreign Application Priority Data

May 15, 1995 [AU] Australia ................. PN2964

[51] Int. Cl.$^6$ ................................................. B28C 7/12
[52] U.S. Cl. ........................... 366/8; 366/17; 366/142
[58] Field of Search .......................... 366/1, 2, 6, 43, 366/44, 8, 53–61, 142, 175.3, 187, 220–231, 601, 17

[56] References Cited

U.S. PATENT DOCUMENTS

| | | | |
|---|---|---|---|
| 2,089,604 | 8/1937 | Hagy | 366/56 X |
| 3,731,909 | 5/1973 | Johnson | 366/61 |
| 4,008,093 | 2/1977 | Kitsuda et al. | 106/89 |
| 4,097,925 | 6/1978 | Butler, Jr. | 366/44 X |
| 4,900,154 | 2/1990 | Waitzinger et al. | 366/56 |

FOREIGN PATENT DOCUMENTS

95/15437   9/1992   WIPO ................. 366/60

*Primary Examiner*—Charles E. Cooley
*Attorney, Agent, or Firm*—William L. Feeney; Kerkam, Stowell, Kondracki & Clarke, P.C.

[57] ABSTRACT

A method and apparatus for mixing concrete in a concrete delivery mixing truck is provided which can yield a mix with an approximate required slump. This is achieved by monitoring the torque loading on hydraulic drive which rotates a mixing barrel and noting an anticipated minimum torque loading which, in turn, approximates to a required slump value. Liquid component is added to a mix until this minimum torque loading is noted. A CPU (17) is used to process information derived from a hydraulic pressure sensor (15) connected in the hydraulic drive motor used to rotate the mixing barrel. A volume/mass input sensor (21) can be used for meaning the amount of particulate ingredients, and a water volume sensor (25) can be used to measure the volume of liquid component added to the mix. When a known maximum volume of liquid component is added a computer can operate to prevent further liquid being added, unless it is purposely overridden. The computer can be used to print a delivery docket via a printer with all the specified concrete data and all the measured parameters, and can also be used to transfer information to a main computer at a concrete depot, so the information can be used as a record of the concrete delivered and also as data for account processing.

15 Claims, 5 Drawing Sheets

METHOD AND APPARATUS FOR MIXING CONCRETE IN A CONCRETE MIXING DEVICE TO A SPECIFIED SLUMP

FIELD OF THE INVENTION

This invention relates to concrete mixing and relates particularly but not exclusively to such for use in connection with mobile concrete mixing trucks.

DESCRIPTION OF PRIOR ART

Hitherto is has been known to use mobile concrete mixing trucks to mix concrete and to deliver that concrete to a site where the concrete may be required. Generally, the particulate concrete ingredients are loaded at a central depot. A certain amount of liquid component may be added at the central depot. Generally the liquid component is added by simply holding a hose or similar into the mixing barrel of the mobile concrete mixing truck. Operators can tell by experience the correct or approximate volume of liquid component each as water to be added according to the volume of the particulate concrete ingredients. The adding of the correct amount of liquid component is therefore usually not precise.

It is known, that if concrete Is mixed with excess liquid component, the resulting concrete mix does not dry with the required structural strength. Accordingly, slump tests have been devised so that a sample of the concrete mix cat be tested with a slump test prior to actual usage on site. Thus, if a concrete mixing track should deliver a concrete mix to a site, and the mix does not have sufficient liquid component, extra liquid component can be added into the mixing barrel of the concrete mixing truck to produce a required slump in a test sample prior to actual delivery of the full contents of the mixing barrel. If excess water is added, the mix will fail the slump test. A problem then exists because it is necessary for the concrete mixing truck to return to the depot in order to add extra particulate concrete ingredients to correct the problem. If these extra particulate ingredients are not added within a relatively short time period after excessive liquid component has been added, then the mix will still not dry with the required strength.

In addition, if excess liquid component has been added, the customer cannot be charged an extra amount for return of the concrete mixing track to the central depot for adding additional particulate concrete ingredients to correct the problem. This, An turn, means that the concrete supply company is not producing concrete economically.

We have determined that the actual driving force to rotate a mixing barrel filled with particulate concrete ingredients and liquid component is directly related to the volume of the liquid component added. In other words, the slump of the mix in the barrel at that time is related to the driving force required to rotate the mixing barrel. We have therefore determined that by monitoring the torque loading on the driving means used to rotate the mixing barrel, the mix can be optimised by adding a sufficient volume of liquid component to attempt to approach a predetermined minimum torque loading related to the amount of the particulate ingredients in the mixing barrel.

When sensors are used to determine the torque loading, the magnitude of the torque sensed can be monitored and the results stored in a store means. The store means can subsequently be accessed to retrieve information therefrom which can be used to, in turn, provide processing of information relating to the mix. In one case, it can be used to provide a report concerning the mixing.

OBJECT AND STATEMENT OF THE INVENTION

Therefore it is an object of the present invention to provide improvements in concrete mixing by noting torque loading required to rotate a mixing barrel.

According to a first aspect of the invention, there is provided a method of mixing concrete comprising:

charging a specified amount of particulate ingredients into a mixing barrel, rotating the mixing barrel by driving means to mix the ingredients, monitoring the torque loading on said driving means used to rotate the mixing barrel, adding a liquid component to wet the mixture and continuing mixing, adding said liquid component in sufficient volume to approach a specified slump of the mix to attempt to approach a predetermined minimum torque loading for the amount of the particulate material in the mixing barrel related to the specified slump, and discharging the wet mix from the mixing barrel.

Preferably said adding of said liquid component is such that the volume of said liquid component added is monitored.

Preferably results of said monitoring of the torque and results of said monitoring of the volume of said liquid component added are stored in a store means and retrievable therefrom.

Preferably said adding is controlled by processing means which predetermines a required volume of liquid component to add to approach said predetermined minimum torque loading and then adding liquid component to the sufficient volume.

According to a second aspect of the invention, there is provided concrete mixing apparatus having a mixing barrel and driving means for rotating said mixing barrel, said driving means having a torque loading sensing means which will monitor the torque loading on said driving means required to rotate said barrel said apparatus permitting said concrete mix to be optimised to approximate a required slump by adding a volume of liquid component to particulate concrete ingredients in said barrel until the monitored torque loading results approach a predetermined minimum torque loading for the amount of particulate material in said barrel and the required slump.

Most preferably said apparatus includes means for monitoring the volume of said liquid component added to the barrel and the monitored results are also, stored in said store means and wherein said results are also retrievable therefrom to provide a report concerning the mixing.

Most preferably processing means is provided to determine the required volume of liquid component to be added to reach the required minimum torque reading.

Preferably said processing means also activates activation means to discharge said liquid component.

Thus, by having sensor means to sense the torque required to rotate the mixing barrel, it is possible to approach a predetermined minimum torque loading for the amount of particulate ingredients by addition of correct volume of liquid component and the resulting mix will have a slump which is generally the required slump for providing the required strength to the concrete.

BRIEF DESCRIPTION OF THE DRAWINGS

In order that the invention can more clearly ascertained examples of preferred embodiments will be described with reference to the accompanying drawings wherein.

DETAILED DESCRIPTION OF PREFERRED EMBODIMENTS

Figure 1:
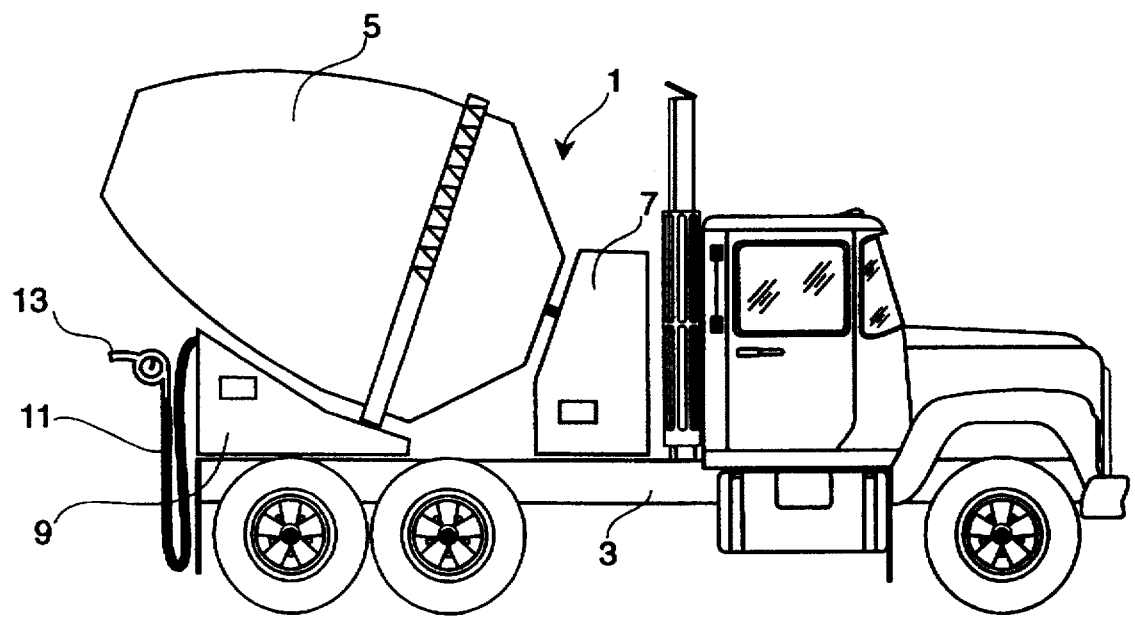
FIG. 1 is a side schematic view of a concrete mixing truck including an example of the present invention.

Referring now to FIG. 1 there is shown a concrete mixing delivery truck 1 of known form. The truck 1 has a prime mover 3 with an inclined mixing barrel 5 mounted thereto so it can rotate about its longitudinal central axis. The mixing barrel 5 is, in turn, rotated by driving means 7 carried by the prime mover 3. The driving means 7 may comprise a chain drive mechanism from a motor means or it may comprise a hydraulic driving means. It will be assumed from hereinafter that the driving means 7 comprises a hydraulic driving means. It could equally comprise a petrol or diesel motor driving means or electric motor driving means. All of these are to be considered within the scope of the invention including any other convenient driving means. The prime mover 3 also carries a supply of liquid component 9 such as water and a hose 11 with a discharge nozzle 13.

The concrete mixing delivery truck 1 can be loaded with particulate concrete ingredients at a central depot. These particulate ingredients may comprise usual components in particulate form for the concrete mix. Accordingly, they may comprise screening, sand, cement, and other additives in a required mix amount. The particulate components are then loaded into the mixing barrel 5 and the amount of the particulate ingredients is noted. This may be by of noting the volume loaded or the mass loaded. Liquid component such as water and/or other additives may be introduced into the mixing barrel 5 at the central depot. Typically, the volume of the liquid component added will be equal to or less than the required amount to provide a correct mix for a required structural strength of any set concrete from the mix.

As stated previously, we have noted that a reduced effort is required to rotate the mixing barrel 5 with increase in added liquid component. Thus, in the case of a hydraulic driving means 7, the hydraulic pressure in the hydraulic driving meals 7 can be monitored and an assessment made, related to the amount of the particulate material An the mixing barrel, as to whether the mix has sufficient liquid component added. In other words, the mix can be optimised by adding a sufficient volume of liquid component to attempt to approach a predetermined minimum torque loading related to the amount of the particulate material in the mixing barrel. This, in turn, will, if achieved, result in the mix having an acceptable slump characteristic. Thus, it is anticipated that concrete which achieves this criteria will dry with the required structural strength.

If the torque loading is measured on the driving means 7 by way of noting the hydraulic pressure in the driving means 7, and it is determined that the mix in the mixing barrel 5 does not have sufficient liquid component then an operator of the concrete mixing delivery truck 1 can remove the nozzle 13 from a holding position and introduce additional liquid component such as water into the mixing barrel. The torque loading on the driving means 7 can be monitored during this addition of liquid component to, in turn, note the hydraulic pressure change. Thus, when the hydraulic pressure reaches a level about at or preferably Just above a predetermined level having regard to the amount of the particulate material in the mixing barrel, it cam be determined that the max will approximately have the required slump characteristics.

We have determined that after particulate concrete ingredients have been added and liquid component added, that a certain time period is required for mixing prior to the mix-stabilising. This, it is desirable not to rely on torque loading monitoring on the driving means 7 until after a time delay occurs for mix-stabilisation.

in the case of a mechanical drive from a motor means to the mixing barrel 5 rather than by a hydraulic coupling, an appropriate load sensing mechanism may be provided in bearings or the like of axles which support gears for pulleys which, in turn, drive the mixing barrel 5. In this way, load sensing may be achieved to monitor the torque loading on the driving means 7. In the case of an electric motor driving means 7, a measure of the electric current drawn can be an indication of the torque loading on the driving means 7. Thus, an appropriate sensing means can be provided to measure the torque loading which, in turn, is related to the force-required to rotate the mixing barrel 5.

Figure 2:
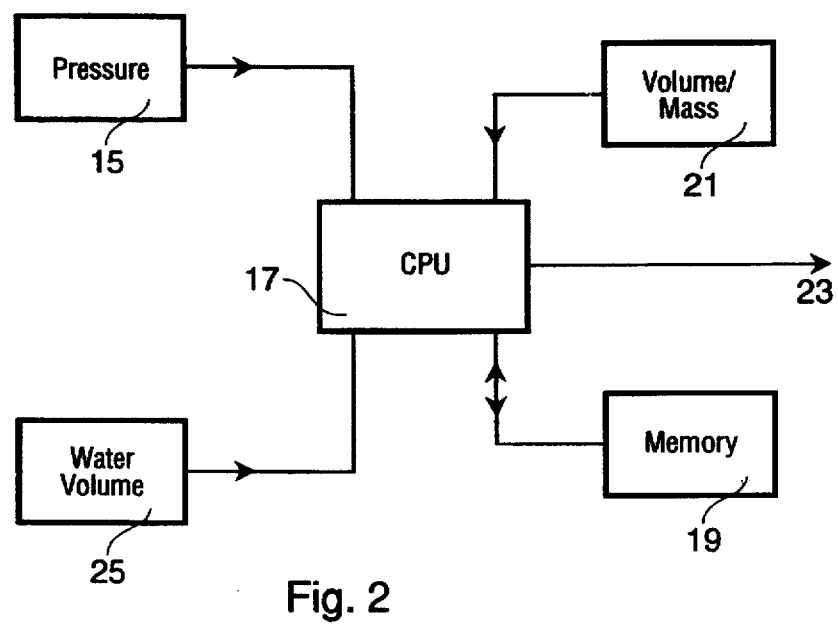
FIG. 2 is a block schematic circuit diagram of sensing means and electric memory means.

Referring now to FIG. 2 there is shown a block circuit diagram of a typical installation provided on a concrete mixing delivery truck 1. A pressure sensor 15 is provided to measure the torque loading on the mixing barrel 5. This pressure sensor may not be a pressure sensor per se but some other sensor which provides a suitable output for the intended purpose. A pressure sensor has been shown for use in connection with a hydraulic driving means 7. The output of the pressure sensor 15 is, in turn, supplied to a central processing unit CPU 17 and the sensed torque loading is, in turn, processed by the CPU 17 and stored in a memory 19. The volume or mass of the particulate concrete ingredients added to the mixing barrel 5 can be inputted via a volume/mass input means 21. This may be entered manually such as through push buttons on a control panel or entered via means of a sensor device associated with the concrete mixing delivery track 1 or from some other sensing means associated with loading of the articulate concrete ingredients into the mixing barrel 5. That information is processed by the CPU 17 and desirable held in the memory 19. The CPU, in turn, processes an hydraulic pressure output which can be monitored. This output is directly related to the torque loading and can be retrievable from the memory 19. The output 23 from CPU 17 may be used to operate a display or alternatively the output from the pressure sensor 15 may be applied to activate a display (not shown) which can be used for noting the torque loading. In this way, liquid component can be added to the mixing barrel 5 to reach or approach a required torque loading as explained previously. The output 23 can be used to provide a report if necessary by extracting the Information retained in the memory 19 relating to the particular mix. FIG. 2 also shows that water volume is sensed by a water volume sensor 25 such as from a volume metering means so that the amount of liquid component added into the mixing barrel 5 is recorded in the memory 19. Thus, the output 23 can contain information relating to the torque loading, the volume or mass of the particulate ingredients, and the water volume added. This, in turn, will provide a permanent record of the mix itself and how the mix progressed until delivery.

The CPU 17 may be arranged to pre-calculate or to otherwise determine a required addition of liquid component to the mix to reach or approach a desired slump which, in turn, can be sensed by noting torque loading on the pressure sensor 15 for the amount of the particulate material. The CPU 17 may therefore have a program step which will open a valve means such as a solenoid valve means which will, in turn, deliver the required additional liquid component as monitored by the water volume sensor 25. Alternatively, instead of opening a valve means, the CPU 17 may be programmed to activate a pump until the required additional liquid component is added as monitored by the water volume sensor 25.

Figure 3:
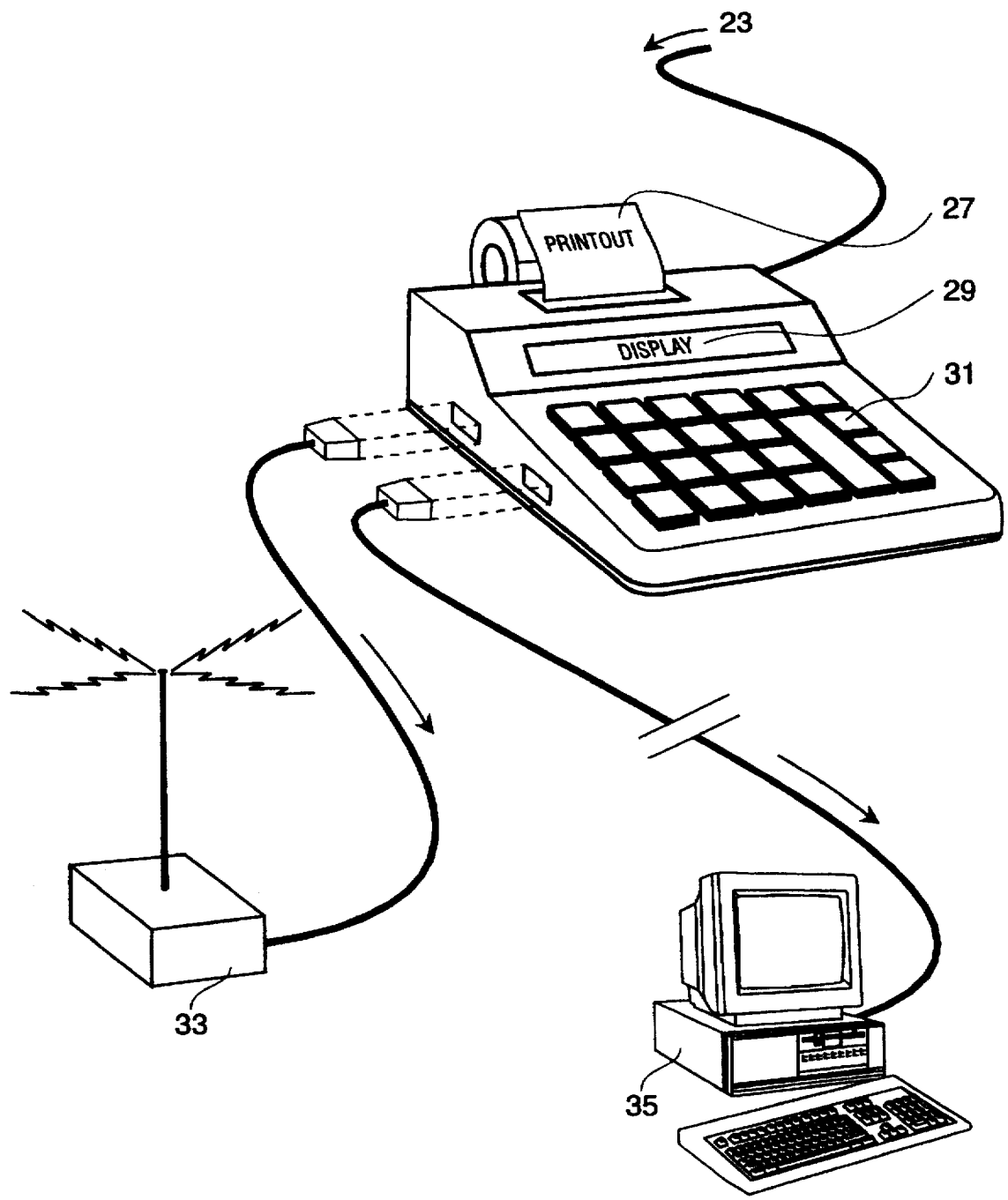
FIG. 3 is a schematic diagram showing use of a hand-held or similar processing device for use in a concrete mixing truck.

FIG. 3 shows how output 23 may be provided to a hand-held device which will provide a printed output report 27 as well as a report on a display screen 29. The hand-held device may have an input panel 31 having a number of push buttons in which information can be input. For example, the volume or mass of the particulate concrete ingredients may be added through the input panel 31. In addition, the particular load or mix details and delivery details can be input through the input panel 31. FIG. 3 shows that the hand-held device may be interconnected with a transmitter 33 to provide radio transmission of the information monitored for the particulate mix. In this way, information relating to the mix can be radioed to the central depot for further processing. In addition, FIG. 3 shows that the held device can be connected to a computer 35, such as a computer at the central depot when the concrete mixing delivery truck i returns. In this way information can be extracted from the hand-held device and used for further processing such as historical record keeping and/or account processing.

Figure 4:
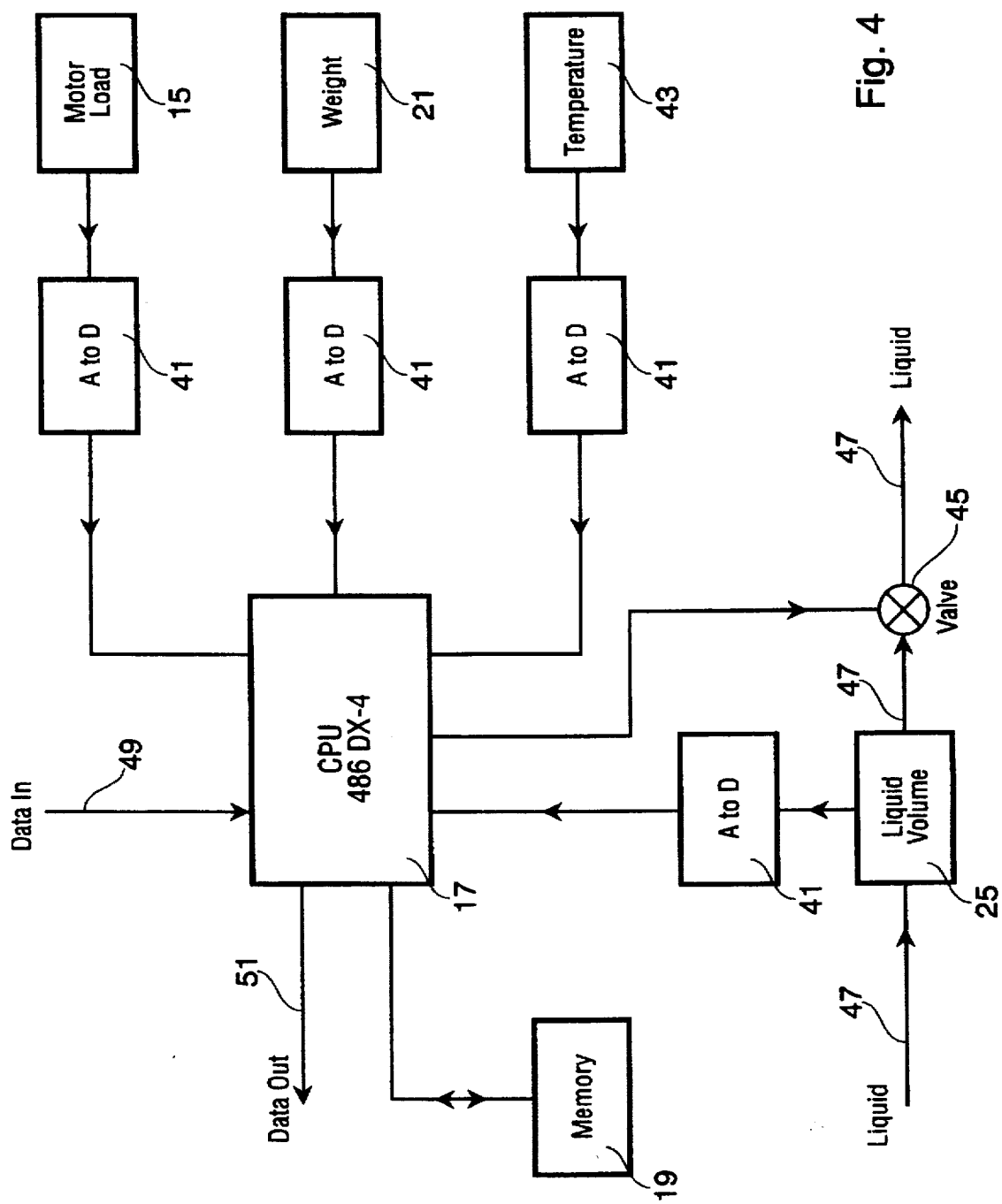
FIG. 4 is a block schematic circuit diagram of a further example similar to that of FIG. 2.

Referring now to FIGS. 4 through 8 there is shown detail of a particularly preferred system. Referring firstly to FIG. 4 there is shown a detailed block circuit diagram of the electronic circuit 17 provided in a concrete mixing truck. Like components to those shown in FIG. 2 are provided with the same numerical designations. In this case, the CPU 17 comprises a standard 486DX4 computer motherboard and has memory 19 in the form of a hard disk connected therewith. The liquid volume sensor 25 connects with the CPU 17 via an A/D converter 41. The weight sensor 21 also connects with the CPU 17 via an A/D converter 41. The motor load sensor 15 in the form of a hydraulic pressure sensor connects with CPU 17 via an A/D converter 41. A temperature sensor 43 is provided to measure air temperature and this is connected with CPU 17 via an A/D converter 41. The A/D converters 41 are 12 bit A/D converters such as type AD14 cards supplied by Industrial Computer Group of 143 Cecil Street, South Melbourne, Victoria, 3205, Australia. The A/D converters 41 provide digital number outputs from 0 to 4095. These outputs are received by the CPU 17 and processed at regular periods. For example, there can he sampling of each of the A/D converters 41 at regular intervals such as, for example, one second intervals, The results of the monitoring of the A/D converters 41 can be held in the memory 19.

A solenoid operated valve 45 is connected with CPU 17 via a driving circuit (not shown). The valve 41 is in a liquid component supply line 47 in series with the liquid volume sensor 25. The solenoid operated valve 45 is used under control of the computer processor 17 to prevent discharge of liquid component when a predetermined amount of livid component has been added to the mix. This function can be overridden by operation of the computer processor 17 by means of a keyboard function but monitoring of information from each of the A/D converts 41 continues In this way, excess liquid component can be inhibited from being added to the mix. If a customer sees the mix and requires extra liquid component to be added then this can be provided for by operation of a keyboard of the computer processor 17 and the amount of extra liquid component added can be monitored and subsequently recorded in memory 19 to provide a record that the customer asked for extra liquid component to be added. In this way, a record can be made and thus responsibility for concrete which does not achieve a required structural strength can be shifted to the customer. The CPU 17 may be arranged to receive data from a data-in line 49 which may be via the keyboard of the counter 17 or via an input port. The recorded information in the memory 19 maybe accessed from a data-out line 51. The data-out line 51 may connect with a printer (not shown in this embodiment) or in addition it may provide an output via a port on the computer 17 to permit information in the memory 19 to be downloaded to a main computer at a concrete depot so that information can be recorded and used for processing at the concrete depot.

Figure 5:
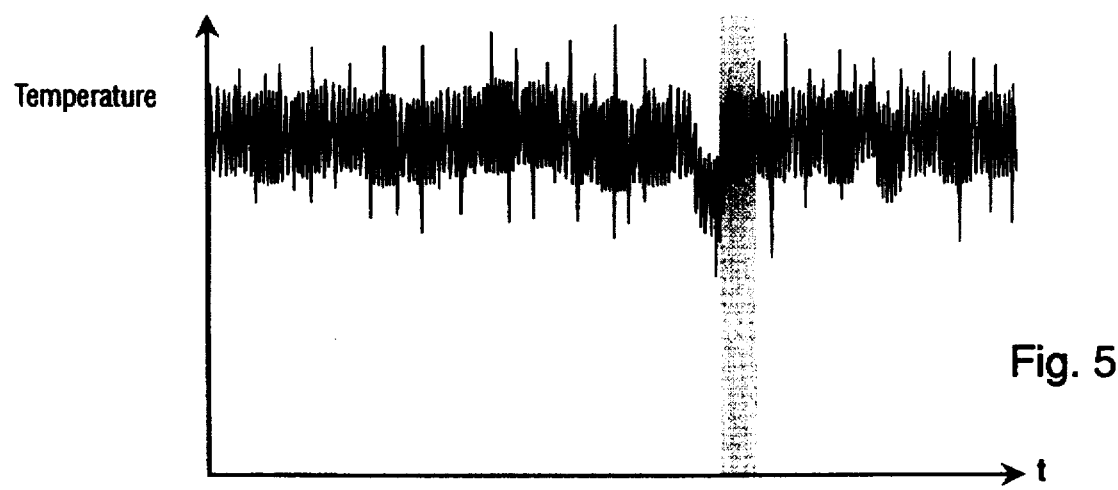
FIG. 5 through 7 are graphs of certain measured valves in the example of FIG. 4.
Figure 6:
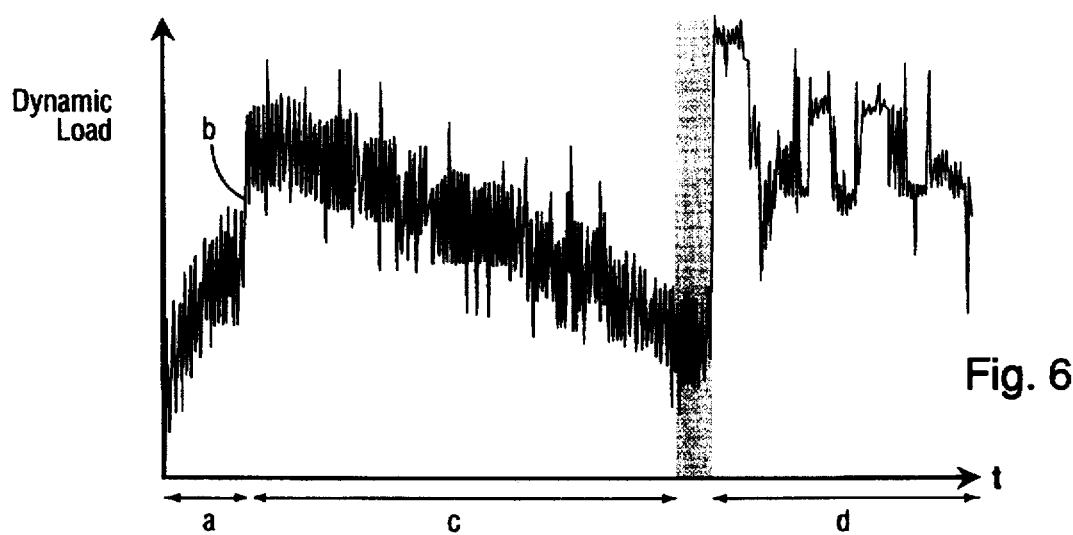
Figure 7:
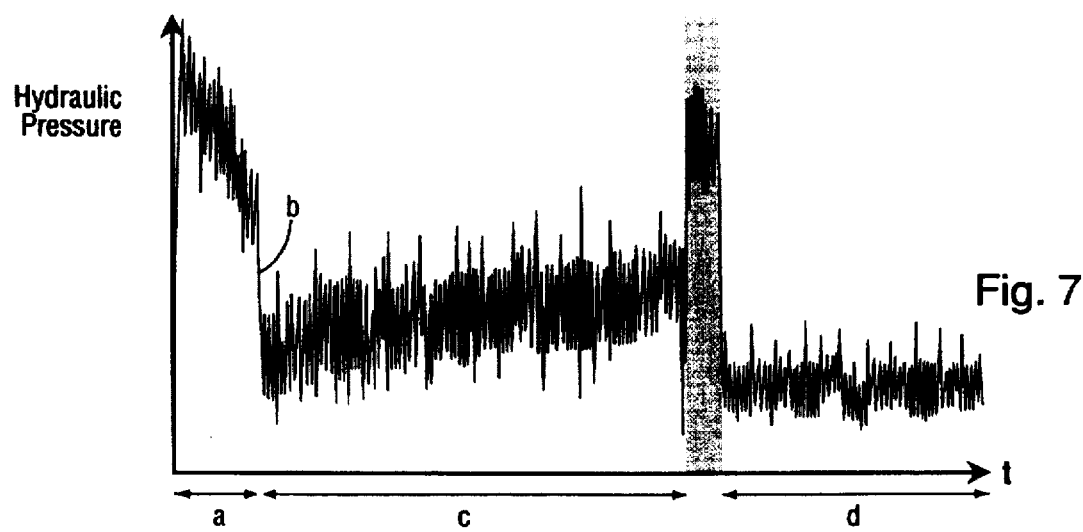

FIGS. 5 through 7 shown graphs of the measured air temperature, the dynamic load on the mixing barrel, and the hydraulic pressure on the mixing barrel driving means, from loading of particulate material ingredients at a concrete depot to actual delivery of the mixed concrete on-site. These graphs will be referred to again in due course.

FIG. 7 clearly shows that the one second intervals of measurement of hydraulic pressure result in a series of pressure steps which are not generally of the same value. Thus, it is necessary to average a series of pressure measurements to arrive at a sample pressure for calculation purposes by the CPU 17. Thus, a mean pressure is established according to the formula:

$$P_{mean} = \frac{P1 + P2 + \ldots P_n}{n}$$

Typically a mean is established over 5 consecutive readings—in this case over a five second period.

It is then necessary to correct the mean pressure reading by a correction factor which is predetermined from calibration of the A/D converter 41 and the actual transducer used. Thus, $P_{actual} mP_{ncan} x(f)$ where f is the correction factor.

A slump value is then calculated as follows:

1. If $P_{actual}$ is less than the digital number 2660, then the following formula is used for slump:

$$slump = 5.26 e^{\left(\frac{5640}{x + \sqrt{x}}\right)}$$

where $x = P_{actual}$

2. If $P_{actual}$ is greater than the digital number 2660 then the following formula is used:

$$slump = \frac{(3660 - P_{actual})}{25}$$

In Australia, slump values are always quoted in multiples of fives. Therefore, the slump value determined by an appropriate one of those formulas is rounded to the nearest 5. The slump values are then used in a computer program running on the processor 17 to determine if the mix is reaching a required slump value when a predetermined slump value is reached for the mix then the computer activates the solenoid valve 41 to prevent the supplied product being wetter than required—excess liquid component is prevented from being added. As stated previously, this can be overridden but only upon the customer's request.

Figure 8:
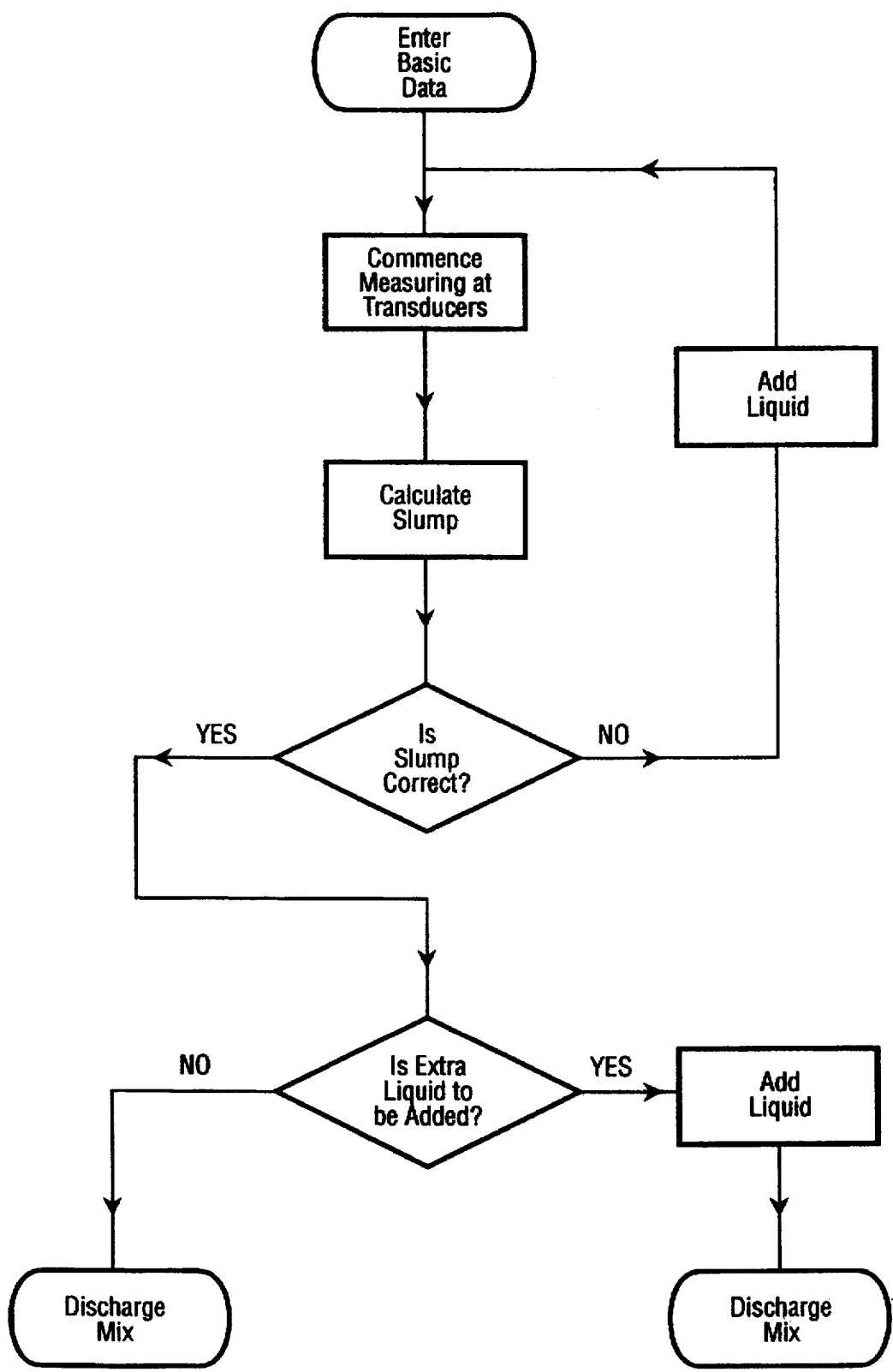
FIG. 8 is a flow diagram of software used in the example of FIG. 4.

Referring now to FIG. 8 there is shown a flow diagram of the process steps used in the processor 17 for determining correct slump. Here, basic data is entered into the computer processor 17. This occurs after the addition of particulate material at the concrete depot and perhaps after addition of liquid component which is added at the concrete depot. The system then commences measuring at each of the transducers comprising the motor load sensor 15, the weight sensor 21, the liquid volume sensor 41 and the temperature sensor 43. A slump is then calculated periodically using the previously described processes. The computer then checks to see if the slump is a correct slump for the amount of ingredients added, and the required specification of concrete. If the slump is not correct then extra liquid component can be added and the process repeated. If the slump is correct then a decision is to be made as to whether extra liquid component is to be added. If, it is not then the mix can be discharged. If it is then the extra liquid component can be added upon request by the customer only. The mix can then be discharged. If extra liquid component is added then the volume of the addition is recorded by the processor 17 as described previously. When the mix has been discharged a delivery docket can be printed from a printer connected with the data-out line 51 to provide a record of the mix and the various parameters measured and stored in the memory 19.

Referring now to the graphs shown in FIGS. 5 through 7 it can be seen that the temperature measurement of FIG. 5 is generally constant. Temperature is measured as this effects the evaporation rate of liquid component and can be used in the processor 17 to modify slump readings having regard to evaporated water content and/or to provide other compensating factors if necessary. The vertical bar shown hatched represents addition of liquid component by an operator of the truck and usually this occurs when the concrete truck arrives on site must prior to delivery. This will be explained further in due course.

Referring now particularly to FIG. 6 there is shown a first region "a" which represents loading of particulate material into the mixing barrel. Some liquid component may be added at this point of time. There is a sudden increase in the dynamic load which occurs at point "b" and is consequent on speeding up the rotation of the mixing barrel. The time period "c" represents the time taken for the mixing truck to travel from the depot to the site. During this mime period the barrel of the mixing truck is rotated at a slow speed and it can be seen that the graph shows a generally decreasing dynamic load sensed by the hydraulic sensor 5. When the trunk arrives on site and concrete is required to be discharged, then liquid component is added as shown by the vertically extending cross-hatch portion on the graph. Liquid component is added to reach an expected slump for the particular mix. The customer my ask for extra liquid component to be added above a pre-set amount, as explained previously. After the liquid component has been added then the mixing barrel reverses its direction and there is a sudden transition with increased loading through region "d" of the graph. This represents discharge of the mix.

It is noted that FIG. 7 approximately mirror images FIG. 6, at least in so far as the loading transitions at "b" and the discharge of the mix at "d". it is also noted that the dynamic load decreases from the concrete depot to the delivery site due to evaporation of water or other liquid component. It is also noted that the hydraulic pressure increases over the same period, indicating that the slump changes from the depot to the delivery site.

The information which can be provided to the computer 17 to the data-in line 49 may include the following:
1. truck number
2. docket number
3. batch water
4. amount of particulate material ingredients required
5. sand moisture content (measured at the depot by a probe into the sand)
6. date
7. time
8. nominated slump
9. product description The above are examples only and are not considered to be exhaustive. This information can be provided in any convenient way. The information is then stored in the memory 19 of the processor 17. The system can then calculate from the inputted information the required liquid component needed to arrive at a desired slump. Alternatively, this may be pre-calculated and loaded into the computer 17 with the other information. The computer 17 may also automatically determine that liquid component needs to be added to maintain a required slump and thus it may automatically discharge liquid component into the mixing barrel 5 by a suitable discharge nozzle (not shown). The volume of the liquid component added can be monitored and stored in the memory 19.

The memory 19 may have an area set aside for storing information in a look-up table related to a range of possible mixes. Thus, for particular mix types and particular slump values and particular amounts of mix ingredients, the system will be able to compare measured values by the sensors against known values for the mix to provide for an adjustment either manually or automatically of the liquid component which is added.

The examples described herein permit improved accuracy to be achieved in relation to delivery of concrete in order to meet specified characteristics of concrete. In addition, the examples enable maximisation of mixing without an oversupply of liquid component which may necessitate return of the concrete mixing delivery truck 1 to the central depot to add additional particulate concrete ingredients to correct any oversupply of liquid component.

Modifications may be made to the invention as would be apparent to persons skilled in the concrete mixing arts and/or engineering arts. These are other modifications may be made without departing from the invention the nature of which is to be determined from the foregoing description.

We claim:

1. A method of mixing concrete comprising:

charging a specified amount of particulate ingredients into a mixing barrel;

rotating the mixing barrel by driving means to mix the ingredients;

monitoring torque loading on said driving means used to rotate the mixing barrel;

adding a liquid component into the mixing barrel to wet the ingredients and continuing mixing to produce a mix;

adding said liquid component in sufficient volume to approach a specified slump for the mix to attempt to approach a predetermined minimum torque loading on said driving means for the amount of the particulate material in the mixing barrel related to the specified slump; and discharging the mix from the mixing barrel.

2. A method as claimed in claim 1 comprising monitoring the volume of said liquid component added.

3. A method as claimed in claim 2 comprising storing results of said monitoring of the volume of said liquid component in a store means so as to be retrievable from said store means.

4. A method as claimed in claim 1 wherein processing means is used to monitor the volume of said liquid component added and to calculate a slump value from a monitored value of torque loading following addition of said liquid component.

5. A method as claimed in claim 4 wherein said processing means operates control means to prevent addition of said liquid component in excess of that needed to achieve said specified slump.

6. Concrete mixing apparatus having a mixing barrel and driving means for rotating said mixing barrel, said driving means having a torque loading sensing means which monitors the torque loading on said driving means required to rotate said barrel, said torque loading sensing means being connected with a processing means programmed to enable a concrete mix in said mixing barrel to be optimized to approximate a required slump by calculating a predetermined minimum torque loading on said driving means for the required slump for an amount of particulate material in said mixing barrel, so that an operator can monitor the torque loading sensed by said torque loading sensing means as liquid component is added to said concrete mix during mixing, and cease adding liquid component when the monitored torque loading sensed by said torque loading sensing means approaches said predetermined minimum torque loading.

7. Apparatus as claimed in claim 6 including means for monitoring the volume of said liquid component added to the barrel and wherein the monitored results are stored in a store means and wherein said results are retrievable from said store means to provide a report concerning the mixing.

8. Apparatus as claimed in claim 7 wherein said processing means is programmed to determine a required volume of liquid component to be added to said barrel to reach said predetermined minimum torque loading for the amount of particulate material in said barrel.

9. Apparatus as claimed in claim 8 wherein said store means stores information relating to the concrete mix provided from said processing means, said information comprising at least:

1. said required slump;
2. said amount of particulate material in said concrete mix, and wherein said store means is accessible to retrieve all of said information to provide a report for a particular mix of concrete.

10. Apparatus as claimed in claim 9 wherein said processing means has a printer and wherein said stored results and said stored information are retrievable as a printed report from said printer.

11. Apparatus as claimed in claim 9 wherein said store means also stores information as to:

3. customer details;
4. mix type;
5. date;
6. time of delivery;
7. water content of said particulate ingredients; and wherein said information is also retrievable from said store means to provide said report.

12. Apparatus as claimed in claim 9 wherein said processing means has an area of memory means configured as a look-up table comparator and wherein information concerning a range of possible mixes is stored in said look-up table comparator and wherein said processing means processes the monitored torque loading and the monitored volume of liquid component added and compares said monitored torque loading and said monitored volume of liquid component against said look-up table information.

13. Apparatus as claimed in claim 8 including a liquid component reservoir from which said liquid component can be discharged.

14. Apparatus as claimed in claim 13 including liquid component control means connected with said processing means to prevent addition of said liquid component above a predetermined volume for the required slump.

15. Apparatus as claimed in claim 7 including a depot with a further processing means and wherein information stored in said store means can be retrieved by said further processing means for processing at said depot.

* * * * *